United States Patent [19]

Jing-Sheng

[11] Patent Number: 4,640,276
[45] Date of Patent: Feb. 3, 1987

[54] SUPER-THIN ENURESIS ALARM

[76] Inventor: Tseng Jing-Sheng, 5 Fl., No. 460-2, Kuang-Fu S. Rd., Taipei, Taiwan

[21] Appl. No.: 714,168

[22] Filed: Mar. 20, 1985

[51] Int. Cl.$^4$ .............................................. A61B 19/00
[52] U.S. Cl. .............................................. 128/138 A
[58] Field of Search .................... 128/138 A; 340/573; 200/DIG. 1

[56] References Cited

U.S. PATENT DOCUMENTS

| | | | |
|---|---|---|---|
| 4,069,817 | 1/1978 | Fenole et al. | 128/138 A |
| 4,106,001 | 8/1978 | Mahoney | 128/138 A |
| 4,205,672 | 6/1980 | Dvorak | 128/138 A |
| 4,271,406 | 6/1981 | Wilson | 128/138 A |
| 4,290,052 | 9/1981 | Eichelberger et al. | 200/DIG. 1 |
| 4,356,479 | 10/1982 | Wilson | 128/138 A |
| 4,506,257 | 3/1985 | Roberts, Sr. | 340/573 |

FOREIGN PATENT DOCUMENTS 95180 11/1983 European Pat. Off. ........ 128/138 A

OTHER PUBLICATIONS

"A Low Cost Portable Enuresis Alarm", by G. Manson et al., J. Med. Eng. and Technol., vol. 3, No. 2, Mar. 1979, pp. 83 and 84.

*Primary Examiner*—Kyle L. Howell
*Assistant Examiner*—David Shay

[57] ABSTRACT

A super-thin enuresis alarm comprising a buzzer case, a printed circuit board, a melody producing integrated circuit and a wet induction conductor can make a musical sound when the diaper in which it is put is wet.

1 Claim, 4 Drawing Figures

SUPER-THIN ENURESIS ALARM

BACKGROUND OF THE INVENTION

1. Field of the Invention

This invention relates to an enuresis alarm which is made 2.7 cm in diameter and 0.5 cm in thickness.

2. Description of the Prior Art

Conventional enuresis alarms are usually complex in their construction, and have separate alarm and extended detector components, such as in U.S. Pat. Nos. 4,069,817 and 4,106,001. Other types, being more simplified in their construction, still comprise two halves of a housing containing an inner poortion with circuit boards therein, such as in U.S. Pat. Nos. 4,271,406 and its continuation case 4,356,479, and European Patent Publication No. 095,180 (Nae Wae Electric Co., Ltd). It is considered that these conventional enuresis alarms have disadvantages in that they are complex in their construction, high in cost, difficult to assemble, and too large for practical use.

SUMMARY OF THE INVENTION

The function of an enuresis alarm is to make a sound when the diaper is wet. The principal object of this invention is thus to provide a super-thin enuresis alarm which comprises a buzzer case, one double sided adhesive tape, and a double sided printed circuit board having a melody producing integrated circuit, and two batteries. The melody producing integrated circuit and two batteries are fitted on the double sided printed circuit board by means of the double sided adhesive tape and the batteries are fixed to the buzzer case.

DETAILED DESCRIPTION OF THE PREFERRED EMBODIMENT

Figure 2:
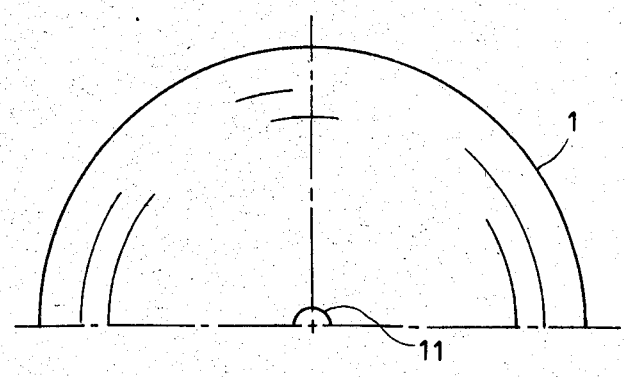
FIG. 2 is a top view of said alarm.
Figure 1:
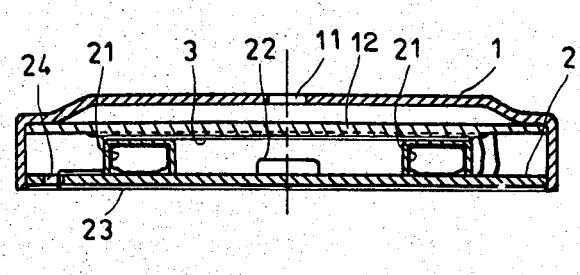
FIG. 1 is a sectional view of the super-thin enuresis alarm of this invention.
Figure 3:
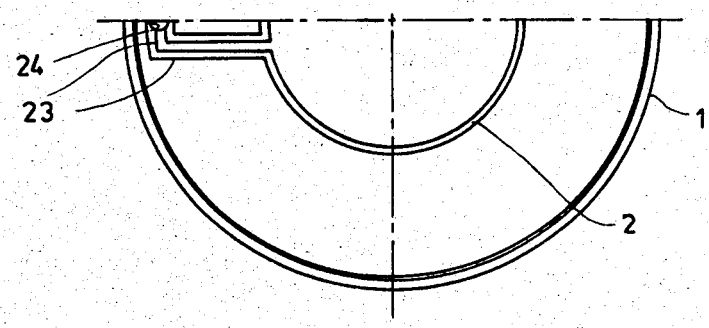
FIG. 3 is a bottom view of said alarm.
Figure 4:
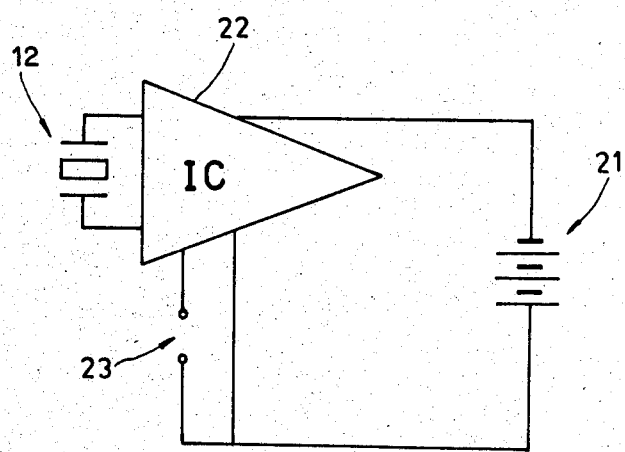
FIG. 4 is a diagram of the printed circuit of this invention.

Referring now to the drawings, the nature of this invention is described as follows:

As shown in FIG. 1, the enuresis alarm 2.7 cm in diameter and 0.5 cm in thickness, is in the form of a super-thin button and is very exquisite and compact. It is very convenient to carry, fix and use. It can be put directly in the diaper or put in a sealed bag and then fixed on the disposable diaper without any electrical cord exposed. So it gives a feeling of safety. The enuresis alarm of this invention comprises a buzzer case 1 having a small sound outlet 11 in the top center, a double-sided printed circuit board 2 having a melody producing integrated circuit 22 on the inside and a wet induction conductor 23 on the outside as shown in FIG. 2 and FIG. 3, two batteries 21 held by battery holders on the printed circuit board 2, and a double adhesive tape 3 to keep the buzzer case 1 firmly on the holders of the batteries 21. The circuit 22 and the conductor 23 are connected through the hole 24 in the printed circuit board 2 as shown in FIG. 4. When the diaper is wet, the electric conductor 23 on the outside will actuate the melody producing integrated circuit 22 to send music signals to the buzzer strip 12 which will make and send out a musical sound through the sound outlet 11.

With a few modifications the alarm can be used as an alarm for preventing the coverlet from being kicked off by a sleeping child or as a cash register alarm or as a touch-on door bell.

Accordingly, the super-thin enuresis alarm is very exquisite, small, compact, safe, durable, practical, and suitable for any kind of diapers and can eliminate all disadvantages of conventional bells.

What is claimed is:

1. A super thin enuresis alarm comprising a buzzer case; double sided adhesive tape; a double sided printed circuit board having a first and a second side; melody producing integrated circuit means; and two batteries; said music producing integrated circuit means and batteries being fitted on said first side of said printed circuit board; said printed circuit board having a hole means therethrough for allowing two parallel conductors to pass from the first side to the second side; said conductors being spatially and electrically separated and having exposed conductive areas to form a switch; said buzzer case having a sound outlet on one side and a buzzer strip on another side; said double sided tape being placed against said buzzer strip; said printed circuit board being placed with said one side, and the batteries and integrated circuit thereon, against said double sided adhesive tape, thereby forming an enclosure containing all of said batteries, melody producing integrated circuit means, and buzzer strip.

* * * * *